US006511972B1

(12) United States Patent
Kofler et al.

(10) Patent No.: US 6,511,972 B1
(45) Date of Patent: Jan. 28, 2003

(54) PHARMACEUTICAL SUSPENSION FORMULATION COMPRISING AMOXYCILLIN CLAVULANIC ACID AND CELLULOSE

(75) Inventors: Bojan Kofler, Stofja Loka (SI); Mateja Kovacic, Ljubljana (SI)

(73) Assignee: LEK Pharmaceutical & Chemical Company D.D., Ljubljana (SI)

( * ) Notice: Subject to any disclaimer, the term of this patent is extended or adjusted under 35 U.S.C. 154(b) by 0 days.

(21) Appl. No.: 09/743,998

(22) PCT Filed: Jul. 15, 1999

(86) PCT No.: PCT/GB99/02295

§ 371 (c)(1),
(2), (4) Date: Mar. 1, 2001

(87) PCT Pub. No.: WO00/03695

PCT Pub. Date: Jan. 27, 2000

(30) Foreign Application Priority Data

Jul. 17, 1998 (GB) ............................................ 9815532

(51) Int. Cl.[7] ...................... A61K 31/43; A61K 31/395; A61K 35/00

(52) U.S. Cl. ................... 514/197; 514/210.06; 424/114

(58) Field of Search ............................ 514/210.06, 197, 514/781; 424/114

(56) References Cited

FOREIGN PATENT DOCUMENTS

| | | |
|---|---|---|
| WO | WO 96/34605 | 11/1996 |
| WO | WO 97/06798 | 2/1997 |
| WO | WO 98/35672 | 8/1998 |
| WO | WO 98/36732 | 8/1998 |

*Primary Examiner*—Rebecca Cook
(74) *Attorney, Agent, or Firm*—Beyer Weaver & Thomas LLP

(57) ABSTRACT

A liquid aqueous pharmaceutical suspension formulation containing as amoxycillin trihydrate, potassium clavulanate and microcrystalline cellulose filler is provided.

12 Claims, No Drawings

PHARMACEUTICAL SUSPENSION FORMULATION COMPRISING AMOXYCILLIN CLAVULANIC ACID AND CELLULOSE

This is a 371 of PCT/GB99/02295 filed Jul. 15, 1999.

This invention relates to liquid aqueous suspension or dispersion formulations, particularly to stable oral pharmaceutical formulations comprising amoxycillin trihydrate and potassium clavulanate. These may be referred to as co-amoxiclav formulations. The invention also relates to the powder formulations for reconstitution as aqueous suspensions, and the granulate formulations for preparation of aqueous dispersions.

Amoxycillin is a well known broad-spectrum semisynthetic betalactam antibiotic effective against many gram-positive and gram-negative microorganisms. In combination with the β-lactamase inhibitor clavulanic acid, amoxycillin is also active against bacterial strains which are normally resistant to betalactam antibiotics. Gastrointestinal intolerance is often reported in patients treated with antibiotics, especially in children and sensitive individuals. Thus, there is the need for developing effective stable pharmaceutical formulations containing amoxycillin and clavulanic acid which have an acceptable taste and reduced gastrointestinal intolerance.

Sugars (such as glucose, fructose, lactose and maltose) and polyols (such as mannitol, sorbitol and xylitol) are often used as excipients in pharmaceutical formulations for preparation of powders for reconstitution as suspensions or granulates for preparation dispersions in water. Sugars and polyols endow the pharmaceutical product with a pleasant taste which is very important in pediatric use. When used in greater quantities as fillers in oral formulations, they have a laxative effect.

In order to minimise gastrointestinal intolerance of the amoxycillin/clavulanic acid suspensions, sugar or mannitol have been replaced with silicon dioxide. However these suspensions have a less pleasant taste.

Attempts have been made to reduce gastrointestinal side effects caused by the drugs containing amoxycillin plus clavulanic acid by using various additives. WO97/07408 discloses amoxycillin/clavulanic acid formualations to which pharmaceutically acceptable organic acid or salts thereof are added to reduce gastrointestinal intolerance. WO97/06798 discloses clavulanate formulations containing pharmaceutically acceptable salts of alkaline earth metals and inorganic acids to minimise gastrointestinal intolerance.

Addition of various metal salts, especially when greater amounts of silicon dioxide are present, potentiates an unpleasant taste making use of such formulations unacceptable.

According to a first aspect of the present invention there is provided a dry powder formulation adapted for reconstitution with water and containing as active ingredients amoxycillin trihydrate and potassium clavulanate, and cellulose as the filler, the formulation optionally further including one or more pharmaceutically acceptable excipients selected from: flavourings, sweeteners, buffering agents, stabilisers, and viscosity modifiers.

In an embodiment the present invention also provides a reconstituted aqueous suspension derived from the dry formulation and containing a unit dosage of active ingredients in 5 ml.

Formulations in accordance with this invention provide an amoxycillin trihydrate/potassium clavulanate powder for reconstitution as a suspension and amoxycillin trihydrate/ potassium clavulanate granulates for preparing dispersions in water for oral administration which have reduced gastrointestinal intolerance and acceptable pleasant taste. The taste of the suspension is especially important in pediatric use. The aim of the invention is achieved by use of cellulose, either microcrystalline or powdered, as a sole filler. Generally other types of celluloses which have greater swelling ability, are used for preparation of suspensions in lower concentrations (0.2 to 5%) acting as viscosity-increasing agent (thickener). Microcrystalline cellulose is used primarily as a diluent in oral tablet and capsule formulations.

Microcrystalline cellulose with a particle size from 20 to 100 μm is preferred. Suitable grades include Avicel types pH 101, 102, 103, 104, 112, 113, 301 and 302. These differ in physical characteristics such as particle size, bulk density, loss on drying, viscosity and chemical characteristics such as the degree of polymerization.

The percentages or amounts referred to in this specification are by weight unless indicated otherwise. Percentages or proportions are selected to total 100%.

In the formulations of this invention, predried cellulose (to reduce free water content which has an unfavourable impact on clavulanic acid stability) used as a filler acting simultaneously as a viscosity-increasing agent and a stabilising agent provides the good stability of the reconstituted suspension over the 7- to 10-day period of use. The amount of cellulose, as a principal filler in the formulation, may range from 5 to 70% w/w, preferably 20 to 70% w/w, more preferably 20 to 60% w/w of the dry formulation. The percentage of the active substances is from 20 to 70%.

Microcrystalline cellulose (Avicel, Emcocel, Vitacel) with an average particle size of 20 μm or preferably microcrystalline cellulose of average particle size of 50 μm may be used. Powdered cellulose (Vivacel, Elcema, SolkaFlok) having different particle size or as granulated powder may be used. In preferred embodiments the microcrystalline cellulose acts as a desiccant to protect the moisture sensitive clavulanate, leading to improved long term stability of the formulation.

Cellulose in the combination with sugars or polyols in the quantities devoid of a laxative effect may be used.

The formulations of this invention may also contain auxiliary ingredients which may be essentially conventional in the art. To improve the taste, flavours and sweetening agents, preferably saccharin, saccharin sodium or aspartame in the amounts allowable for oral formulations may be added. Flavours which may be used may comprise common flavours like strawberry, cherry, wild cherry, lemon, banana, raspberry, orange, caramel or mixtures thereof, which in combination with the antibiotic provide a pleasant flavour and taste.

Suitable excipients may include buffering agents such as different acids and their salts, eg citric acid, sodium citrate, succinic acid, swelling agents and viscosity-increasing agents such as suspension stabilisers and other additives.

The formulations of present invention are suitable for BID or TID administration in the prescribed dose. They are indicated in the treatment of children, adults and the elderly, and patients with difficulty in swallowing.

The present formulations relate to the combination of clavulanic acid and amoxycillin in a weight ratio of 1:1 to 1:20, preferably from 1:4 and 1:8. The formulations relate to the powder for suspension or granulation for dispersion in water for oral administration in the following doses:

| Amoxycillin | Clavulanic acid |
|---|---|
| 125 mg/5 ml | 31.25 mg/5 ml |
| 250 mg/5 ml | 62.5 mg/5 ml |
| 200 mg/5 ml | 28.5 mg/5 ml |
| 400 mg/5 ml | 57 mg/5 ml |
| 600 mg/5 ml | 42.9 mg/5 ml |
| 300 mg/5 ml | 21.45 mg/5 ml |

Other dosages may also be used.

The powder or the granulation should be stored in air-tight screwcap bottles or plastic containers or in sachets for preparation of suspension or dispersion, respectively, immediately prior to use.

The formulations of the present invention can be produced using the conventional manufacturing procedures such as homogenisation, sieving and milling. A portion of the ingredients may be pre-granulated, or granulated ingredients are used to improve powder flowability, which is especially important for sachet packaging.

Predried or anhydrous ingredients should be used in the formulation. Cellulose or a combination of cellulose and sodium carboxymethylcellulose should be dried in tray or vacuum dryers to LOD less than 1%. Additional drying of the ingredients yields the powder and or granulate respectively, with a low moisture content, eg below 6%.

Clavulanic acid and salts thereof are extremely sensitive to the presence of moisture and free water and undergo rapid hydrolytic degradation. Therefor, the formulations of this invention should be manufactured in suitable air-conditioned production areas with relative humidity (RH) less than 30% and temperature below 25° C.

The invention is further described by means of example, but not in any imitative sense.

EXAMPLE 1

Four formulations of this invention with different assays of amoxycillin trihydrate and potassium clavulanate were prepared. Their compositions and the role of individual auxiliary substances are listed in the table below:

| Ingredient | A mg/5 ml | B mg/5 ml | C mg/5 ml | D mg/5 ml |
|---|---|---|---|---|
| Amoxycillin in the form of trihydrate) - active substance | 400.00 | 200.00 | 600.00 | 300.00 |
| Clavulanic acid (in the form of potassium salt) - active substance | 57.00 | 28.50 | 42.90 | 21.45 |
| Citric acid - buffering agent | 2.69 | 2.69 | 2.69 | 2.69 |
| Sodium citrate - buffering agent | 8.33 | 8.33 | 8.33 | 8.33 |
| Microcrystalline cellulose and sodium carboxymethylcellulose - viscosity-increasing agent | 28.10 | 28.10 | 28.10 | 28.10 |
| Gum xanthan - viscosity-increasing agent | 10.00 | 10.00 | 10.00 | 10.00 |
| Colloidal silicon dioxide | 16.67 | 16.67 | 16.67 | 16.17 |
| Silicon dioxide - thickener | 216.60 | 216.60 | 216.60 | 216.60 |

-continued

| Ingredient | A mg/5 ml | B mg/5 ml | C mg/5 ml | D mg/5 ml |
|---|---|---|---|---|
| Flavours, eg strawberry | 13.30 | 13.30 | 13.30 | 13.30 |
| caramel | 15.00 | 15.00 | 15.00 | 15.00 |
| Sweetening agent, eg saccharin sodium | 6.70 | 6.70 | 6.70 | 6.70 |
| Cellulose (microcrystalline or powdered) - filler | to 1250.00 | to 1000.00 | 1250.00 | 1000.00 |

EXAMPLE 2

The following formulations were prepared conventionally as dry powder mixtures.

| Ingredient | E mg/5 ml | F mg/5 ml |
|---|---|---|
| Amoxycillin (in the form of trihydrate | 250.00 | 125.00 |
| Clavulanic acid (in the form of potassium salt) | 62.50 | 31.25 |
| Citric acid | 3.00 | 3.00 |
| Sodiuim citrate | 9.00 | 9.00 |
| Microcrystalline cellulose and sodium carboxymethylcellulose | 13.75 | 13.75 |
| Gum xanthan | 11.50 | 11.50 |
| Colloidal silicon dioxide | 9.00 | 9.00 |
| Silicon dioxide | 50.00 | 33.50 |
| Flavours, eg strawberry, caramel | 33.50 | 33.50 |
| Saccharin sodium | 5.00 | 5.00 |
| Cellulose (microcrystalline or powdered) | to 1000 | to 1000 |

These formulations were manufactured using the standard methods known in the art for the production of powders and granulations for reconstitution in an aqueous suspension or for preparing a dispersion in water.

The quantities of inactive ingredients listed may vary from formulation to formulation to achieve the most favourable composition of properties including taste, physical and chemical stability.

Various amounts and types of flavours as well as their combination may be used to achieve optimal taste and odour.

The results of 3 months' accelerated stability testing at 40° C. and 75% rel. humidity showed that the formulation with cellulose as the main diluent proved to have good stability in powder form as well as a reconstituted suspension.

What is claimed is:

1. A dry formulation adapted for reconstitution with water, comprising:

amoxycillin trihydrate and potassium clavulanate active ingredients; and microcrystalline cellulose filler, said microcrystalline cellulose being at least 20% of the weight of the dry formulation.

2. The formulation as claimed in claim 1, further comprising a powdered cellulose.

3. The formulation as claimed in claim 1, wherein the amount of microcrystalline cellulose is 20 to 70% by weight of the dry formulation.

4. The formulation as claimed in claim 1, wherein the amount of active ingredients are 20 to 70% by weight of the dry formulation.

5. The formulation as claimed in claim 1, wherein the microcrystalline cellulose has an average particle size of 50 μm.

6. The formulation as claimed in claim 1, wherein the ratio between amoxycillin trihydrate and potassium clavulanate is between 1:1 to 20:1, the weights being between expressed as the free parent acids amoxycillin and clavulanic acid.

7. A reconstructed aqueous suspensions or dispersion, comprising:

water;

amoxycillin trihydrate and potassium clavulanate active ingredients; and microcrystalline cellulose filler, said microcrystalline cellulose being greater than 20% of the dry weight of the active ingredients and filler.

8. A method for treatment of bacterial infections in a pediatric or adult patient, comprising:

administration to a patient in need thereof of an effective amount of a formulation comprising:

water;

amoxycillin trihydrate and potassium clavulanate active ingredients; and microcrystalline cellulose filler, said microcrystalline cellulose being greater than 20% of the dry weight of the active ingredients and filler.

9. The formulation as claimed in claim 6, wherein the ratio between amoxycillin trihydrate and potassium clavulanate is 7:1, the weights being expressed as the free parent acids amoxycillin and clavulanic acid.

10. The formulation as claimed in claim 6, wherein the ratio between amoxycillin trihydrate and potassium clavulanate is 14:1, the weights being expressed as the free parent acids amoxycillin and clavulanic acid.

11. The formulation as claimed in claim 1, wherein the amount of cellulose is 20 to 60% by weight of the dry formulation.

12. The formulation as claimed in claim 1, wherein the amount of cellulose is 35 to 50% by weight of the dry formulation.

* * * * *